United States Patent [19]

Dennehey

[11] 4,294,250
[45] Oct. 13, 1981

[54] LUER LOCK CONNECTION DEVICE

[75] Inventor: T. Michael Dennehey, Arlington Heights, Ill.

[73] Assignee: Baxter Travenol Laboratories, Inc., Deerfield, Ill.

[21] Appl. No.: 101,246

[22] Filed: Dec. 7, 1979

[51] Int. Cl.³ .............................................. A61M 3/00
[52] U.S. Cl. ................................................... 128/247
[58] Field of Search ............... 128/247, 213 R, 213 A, 128/214 R, 214 C, 214 D, 214 E, 214 F, 215, 216, 272.3; 285/332

[56] References Cited

U.S. PATENT DOCUMENTS

| 3,394,954 | 7/1968 | Sarns | 128/247 X |
| 4,076,285 | 2/1978 | Martinez | 128/247 X |
| 4,133,312 | 1/1979 | Burd | 128/247 |
| 4,187,848 | 2/1980 | Taylor | 128/247 |

FOREIGN PATENT DOCUMENTS 994631  8/1976  Canada ............................... 128/247

*Primary Examiner*—John D. Yasko
*Attorney, Agent, or Firm*—Paul C. Flattery; George H. Gerstman

[57] ABSTRACT

A luer lock connection device for medical use, for example, in continuous ambulatory peritoneal dialysis in which a solution container is coupled via flexible tubing to a patient's tube that communicates with the patient's peritoneal cavity.

The luer lock connection device includes a cooperating male luer lock connector and a female luer lock connector, with visual indicating means provided to indicate that the male and female connectors are assembled properly for use when they are in a predetermined relationship. The male and female luer lock connectors are structured to provide a double sealing arrangement for aiding in maintaining an uncontaminated connection.

12 Claims, 10 Drawing Figures

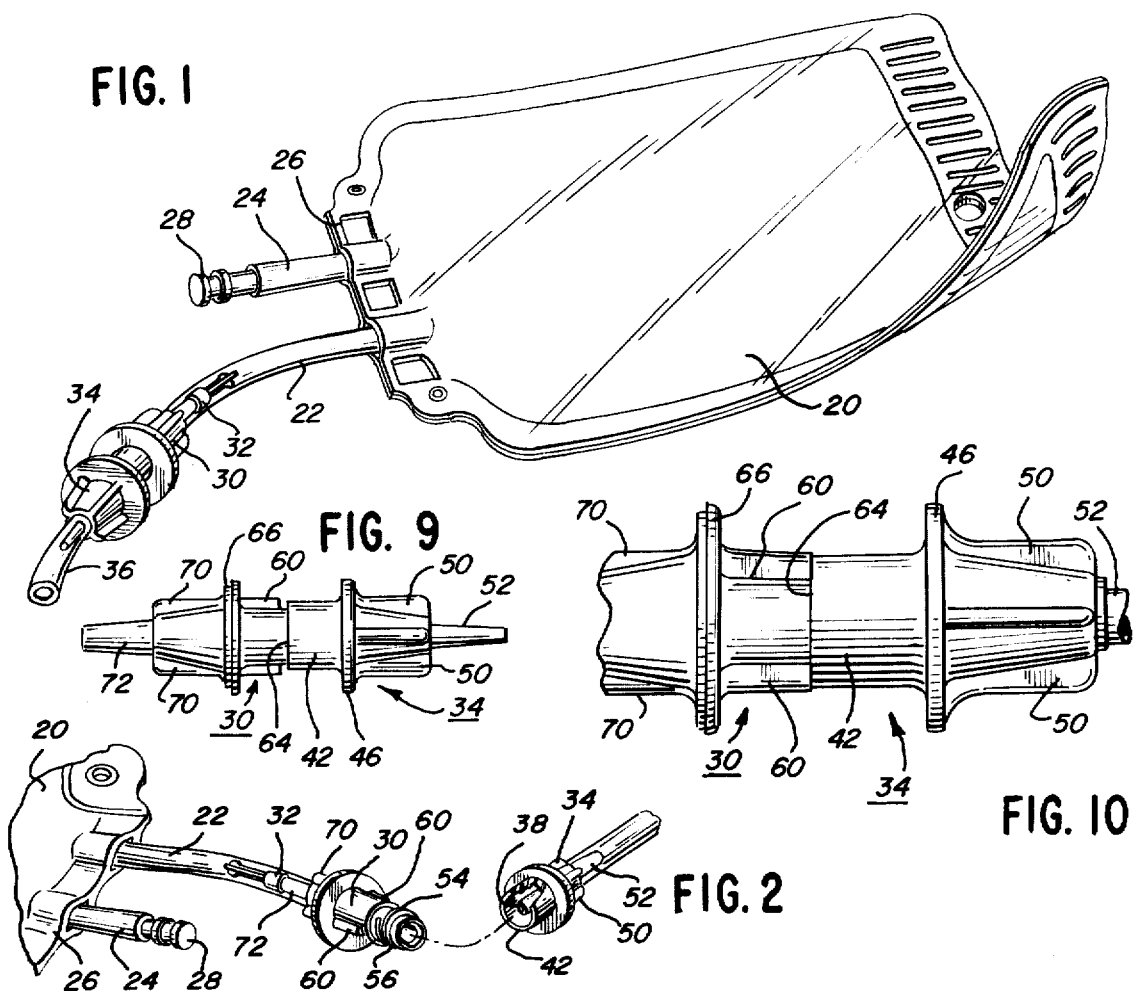
FIG. 1
FIG. 9
FIG. 10
FIG. 2
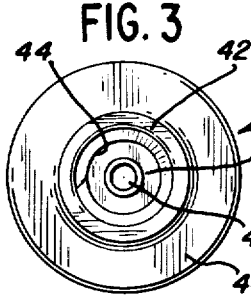
FIG. 3
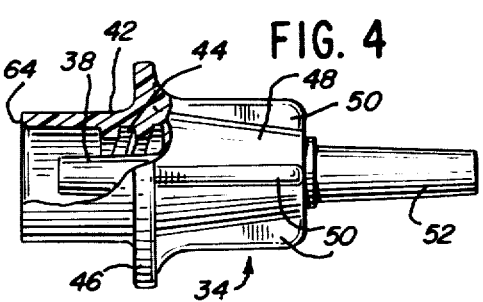
FIG. 4
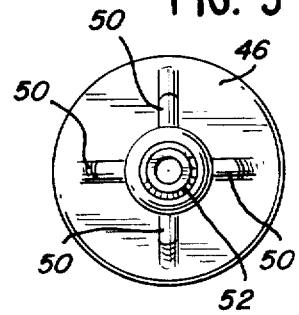
FIG. 5
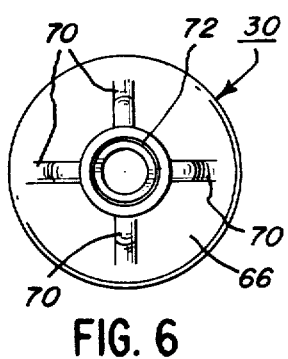
FIG. 6
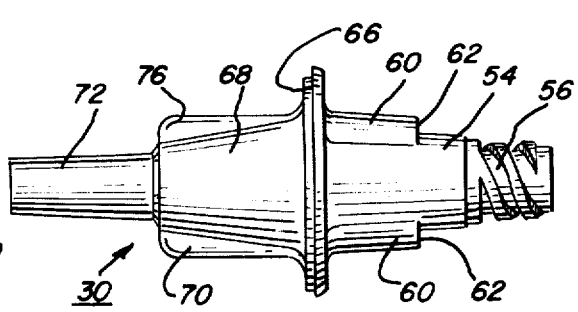
FIG. 7
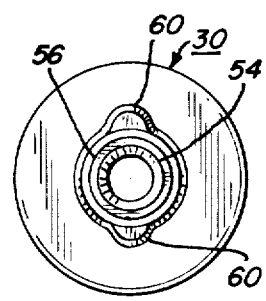
FIG. 8

LUER LOCK CONNECTION DEVICE

BACKGROUND OF THE INVENTION

This invention concerns a novel luer lock connection device, and more particularly, a luer connection device that may be used in continuous ambulatory peritoneal dialysis. It is to be understood, however, that the novel luer lock connection device of the present invention is suitable for use in other medical applications.

In continuous ambulatory peritoneal dialysis, a dialysis solution is introduced to the peritoneal cavity of the patient, allowed to remain there for several hours and then drained from the patient's peritoneal cavity with this process being repeated on a substantially continuous basis. One manner of achieving this type of dialysis is described in a pending application in the names of T. Michael Dennehey, Richard J. Greff and Ludwig Wolf, Jr., filed in the U.S. Patent and Trademark Office on Jan. 23, 1979, Ser. No. 5,748 and entitled "Solution Container For Continuous Ambulatory Peritoneal Dialysis".

One manner of achieving continuous ambulatory peritoneal dialysis includes the steps of connecting a dialysis solution container to a catheter connected to the patient's peritoneal cavity, unclamping the tubing between the dialy solution container and the patient's peritoneal cavity so as to allow the dialysis solution to flow from the container to the peritoneal cavity, thereafter reclamping the tubing, allowing the dialysis solution to remain within the patient's peritoneal cavity for several hours, for example, four hours, unclamping the tubing and draining the solution from the patient's peritoneal cavity back to the dialysis solution container, disconnecting the dialysis solution container from the catheter tube and connecting to the catheter tube a fresh dialysis solution container, and repeating the aforementioned steps. In the above-mentioned pending patent application Ser. No. 5,748, a connection and disconnection system between the dialysis solution container and the patient's catheter tube described as being achieved by using a luer lick connector system. To this end, the transfer tube extending from the dialysis solution container carries a first luer connector and the catheter tube extending from the patient's peritoneal cavity carries a complementary luer lock connector. In order to prevent peritonitis from occurring, it is extremely desirable to achieve and maintain an uncontaminated connection at the luer connector.

It is, therefore, an object of the present invention to provide a luer lock connection device that has the ability to achieve and maintain an uncontaminated connection.

Another object of the present invention is to provide a luer lock connection device that is simple in construction and is efficient to manufacture.

A further object of the present invention is to provide a luer lock connection device that offers a double seal at the connection.

A still further object of the present invention is to provide a luer lock connection device which provides visual means for the user to identify when the connectors are assembled properly for use.

Other objects and advantages of the present invention will become apparent as the description proceeds.

SUMMARY OF THE INVENTION

In accordance with the present invention, a luer lock connection device is provided which comprises a cooperating male luer lock connector and a female luer lock connector. The male luer lock connector has a central tubular portion which defines an axial bore with at least a portion of the central tubular portion being enclosed by an outer sheath having a generally circular cross-sectional configuration. The outer sheath has internal connecting means for cooperating with external connecting means of the female luer lock connector.

The female luer lock connector comprises a main tubular member for receiving the central tubular portion and having external connecting means for cooperating with the internal connecting means of the male connector's outer sheath. The main tubular member of the female luer connector has visual indicating means which is positioned to indicate that the male and female connectors are assembled properly for use when the outer sheath and the visual indicating means are in a predetermined relationship.

In the illustrative embodiment, the visual indicating means comprises an outwardly extending member adapted for engagement with the outer sheath when the male and female connectors are assembled properly.

In the illustrative embodiment, the external surface of the central tubular portion of the male luer lock connector is adapted to form a sealing engagement with the internal wall of the main tubular member of the female luer lock connector. Further, the external surface of the female luer lock connector is adapted to form a sealing engagement with the internal wall of the outer sheath. In this manner, a double seal is provided.

In the illustrative embodiment, the predetermined relationship between the outer sheath and the outwardly extending member is an abutting relationship which comprises an overdriven position of the main tubular member with respect to the central tubular portion.

A more detailed explanation of the invention is provided in the following description and claims, and is illustrated in the accompanying drawings.

BRIEF DESCRIPTION OF THE DRAWINGS

FIG. 1 is a perspective view of a dialysis solution container and further illustrating a luer lock connection device constructed in accordance with the principles of the present invention;

FIG. 2 is a perspective view of a cooperating male luer lock connector and a cooperating female luer lock connector constructed in accordance with the principles of the present invention;

FIG. 3 is a front view of a male luer lock connector constructed in accordance with the principles of the present invention;

FIG. 4 is a side elevational view thereof, with portions broken away for clarity;

FIG. 5 is a rear view thereof;

FIG. 6 is a rear view of a female luer lock connector constructed in accordance with the principles of the present invention;

FIG. 7 is a side elevational view thereof;

FIG. 8 is a front view thereof;

FIG. 9 is a side view of the male and female luer lock connectors in a position where they are being assembled for use; and FIG. 10 is a side view of the luer lock connectors, similar to the view of FIG. 9 but showing the luer lock connectors assembled properly for use.

DETAILED DESCRIPTION OF THE ILLUSTRATIVE EMBODIMENT

Referring to FIGS. 1 and 2, a dialysis solution bag 20 is shown therein having ports 22 and 24 extending from one side 26 of the bag 20. Port 24 is capped with an injection site 28 in the illustrative embodiment.

Solution container 20 is preferably formed of flexible sheet plastic material that is heat sealed at its edges to form a solution bag. Port 22 includes flexible plastic tubing which has a female luer lock connector 30 at its distal end. A frangible member 32 is positioned in series with transfer port 22 and female luer lock connector 30, within the bore defined by the flexible tubing. Frangible member 32 blocks fluid flow from the transfer port until the frangible member 32 is broken. Frangible member 32 is preferably formed of a plastic material which fills the flow path of the transfer port and tubing 22, but defines a central bore through the plastic material whcih is sealed by a break-off member. When the break-off member is manually broken, the dialysis solution contained by solution container 20 can flow through the frangible member 32 and downstream with respect thereto. In this manner, the dialysis solution within solution container 20 is maintained adjacent transfer port 22 until frangible member 32 is broken, and not until the breaking of frangible member 32 can the solution contained within solution container 20 flow downstream of the frangible member 32.

Female luer lock connector 30 is connected to a male luer lock connector 34 which is carried at the distal end of a patient's catheter tube 36 which is coupled to the patient's peritoneal cavity. Additional details concerning the construction of the novel luer lock connection system formed by female luer lock connector 30 and male luer lock connector 34 are set forth below and are illustrated in FIGS. 2-10.

Male luer connector 34 is illustrated in detail in FIGS. 3-5. Referring to these Figures, the male luer connector 34 comprises a central tubular portion 38 defining an axial bore 40, with the central tubular portion 38 tapering outwardly rearwardly to a certain location and then not tapering rearwardly of that certain location. As a specific example, although no limitation is intended, central tubular portion 38 tapers outwardly from its front end to a point 0.25 inch rearwardly therefrom, and the further rearward portion of the central tubular member 38 beginning at break-point 45 is not tapered.

Central tubular portion 38 is enclosed by an outer sheath 42 having a generally circular cross-sectional configuration. Outer sheath 42 is internally threaded with threads 44, which threadedly cooperate with external threads of a female luer connector as will be described. The outer sheath 42 aids in preventing touch contamination during locking and/or unlocking of the luer lock connection system and serves to carry the threads 44 which are engaged by the external threads carried by the female luer lock connector 30.

Male luer lick connector 34 carries a radially extending flange 46 and a graspable body portion 48 having equally spaced outwardly extending members 50 which aid in enabling the operator to grasp body portion 48. A rear coupling member 52, which is coaxial with central tubular portion 38, is provided for coupling the male luer connector with flexible plastic tubing 36, by solvent bonding or other means known in the art.

Referring to FIGS. 6-8 in which the female luer lock connector 30 is shown in detail, it can be seen that connector 30 comprises a main tubular member 54 having an externally threaded front portion 56. Threaded portion 56 is dimensioned for threaded engagement with internal threads 44 of the male luer connector 34. Main tubular member 54 is tapered outwardly rearwardly so as to form a sealing engagement with the internal wall of outer sheath 42. Thus as threaded portions 56 and 44 are screwed together, the internal wall of outer sheath 42 will ride along the outwardly tapering external surface of main tubular member 54, providing an effective seal. It is preferred that the male and female luer lock connectors be formed of a relatively resilient material, such as an elastomeric material. As a specific example, although no limitation is intended, a material such as polyester PL-1109 may be used.

Maine tubular member 54 carries visual indicating means 60 in the form of outwardly extending ribs, each having a front end 62 which is adapted to abut the front end 64 of the outer sheath 42 when the male and female connectors are assembled properly for use. Female luer lock connector 30 has a radially extending circular flange 66 and a rear body portion 68 for grasping by the operator similar in construction to rear body portion 48 of male luer connector 34. Likewise, female luer lock connector 30 carries four outwardly extending members 70 which are similar in construction to members 50 of the luer lock connector 34 and a rearwardly extending coupling member 72 which is similar to coupling member 52 of the male luer connector 34.

The coupling of the male luer connector 34 to the female luer connector 30 is most clearly illustrated in FIGS. 2, 9 and 10. When the male and female connectors are assembled, the external threads 56 engage the internal threads 44 and as the connectors are screwed together, central tubular portion 38 is received within the bore defined by main tubular member 54, with a seal being provided by the time that the internal wall of main tubular member 54 is engaging the end of the tapered portion of the external surface of central tubular portion 38. At the same time, a double seal is being provided because the internal wall of outer sheath 42 forms a sealing engagement with the outwardly flared external wall of main tubular member 54. Thus the double seal is provided when the male and female connectors are in the general position illustrated in FIG. 9. However, in order to ensure the maintenance of the double seal, the user continues to screw the connectors together until front end 64 of the outer sheath 42 abuts ends 62 of ribs 60, as illustrated in FIG. 10. Thus the sealing area between the external surface of central tubular portion 38 and the internal wall of main tubular member 54 is physically overdriven and additional amount, which in the illustrative embodiment may be 1/16th inch. Because one or both members are formed of an elastomeric material, accommodation takes place between the parts and the inner seal is not compromised. By not continuing the luer taper, the taper ending at break-point 45 interference between the parts is reduced and this reduction in interference assists in accomplishing the overdrive feature without compromising the inner seal. At the same time, the visual indicator provided by the abutment of front end 64 with ends 62 provides the user with a visual verification that the connectors are properly assembled. No sense of touch or tightness of connection is needed.

Although an illustrative embodiment of the invention has been shown and described, it is to be understood that various modifications and substitutions may be made without departing from the novel spirit and scope of the present invention. For example, an elastomeric material may be used to form only one of the connectors. While the use of screw threads offers the convenience in drawing and holding the two units together, a bayonet system may be employed to hold the units together. The rib or ribs used as visual indicators could be of other configurations, such as a raised ring. Further, the term "luer" as used herein connotes not only connectors having conventional "luer" tapers, but also connectors having different or no tapers.

What is claimed is:

1. A luer lock connection device which comprises: a cooperating male luer lock connector and a female luer lock connector;
    said male luer lock connector having a central tubular portion defining an axial bore with at least a portion of said central tubular portion being enclosed by an outer sheath having a generally circular cross-sectional configuration;
    said outer sheath having internal connecting means for cooperating with external connecting means of said female luer lock connector;
    said female luer lock connector comprising a main tubular member for receiving said central tubular portion and having said external connecting means for cooperating with the internal connecting means of said male luer connector's outer sheath; and
    said main tubular member of said female luer connector having visual indicating means which is positioned to indicate that the male and female connectors are assembled properly for use when said outer sheath and said visual indicating means are in a predetermined relationship.

2. A luer lock connection device as described in claim 1, said visual indicating means comprising an outwardly extending member adapted for engagement with said outer sheath when said male and female connectors are assembled properly.

3. A luer lock connection device as described in claim 2, said outwardly extending member comprising an external rib having an end thereof adapted to abut the front end of said outer sheath when said male and female connectors are assembled properly.

4. A luer lock connection device as described in claim 1, said internal connection means comprising an internally threaded portion; and said external connection means comprising external threads for threaded cooperation with said internally threaded portion.

5. A luer lock connection device as described in claim 1, said central tubular portion of said male luer lock connector being tapered outwardly rearwardly to form a sealing engagement with the internal wall of said main tubular member of said female luer lock connector.

6. A luer lock connection device as described in claim 5, the external surface of said female luer lock connector being tapered outwardly rearwardly to form a sealing engagement with the internal wall ofr saod outer sheath.

7. A luer lock connection device as described in claim 1, the external surface of said central tubular portion of said male luer lock connector being adapted to form a sealing engagement with the internal wall of said main tubular member of said female luer lock connector; and the external surface of said female luer lock connector being adapted to form a sealing engagement with the internal wall of said outer sheath.

8. A luer lock connection device as described in claim 7, said predetermined relationship comprising an overdriven position of said main tubular member with respect to said central tubular portion.

9. A luer lock connection device as described in claim 8, said central tubular portion being tapered outwardly rearwardly to form a sealing area with said main tubular member but having no taper at an area corresponding to the overdriven position area.

10. A luer lock connection device which comprises:
    a cooperating male luer lock connector and a female luer lock connector;
    said male luer lock connector having a central tubular portion defining an axial bore with at least a portion of said central tubular portion being enclosed by an outer sheath having a generally circular cross-sectional configuration;
    said outer sheath having internal connecting means for cooperating with external connnecting means of said female luer lock connector;
    said female luer lock connector comprising a main tubular member for receiving said central tubular portion and having said external connecting means for cooperating with the internal connecting means of said male luer lock connector's outer sheath;
    the external surface of said central tubular portion of said male luer lock connector being adapted to form a sealing engagement with the internal wall of said main tubular member of said female luer lock connector;
    the external surface of said female luer lock connector being adapted to form a sealing engagement with the internal wall of said outer sheath; and
    said main tubular member of said female luer lock connector having visual indicating means which is positioned to indicate that the male and female connectors are assembled properly for use when said outer sheath and said visual indicating means are in a predetermined relationship, said visual indicating means comprising an external rib having an end thereof adapted to abut the front end of said outer sheath.

11. A luer lock connection device as described in claim 10, said internal connection means comprising an internally threaded portion and said external connection means comprising external threads for threaded cooperation with said internally threaded portion; said central tubular portion being tapered outwardly rearwardly to form a sealing engagement with the internal wall of said main tubular member of said female luer lock connector; and the external surface of said female luer lock connector being tapered outwardly rearwardly to form a sealing engagement with the internal wall of said outer sheath.

12. A luer lock connection device which comprises:
    a cooperating male luer lock connector and a female luer lock connector;
    said male luer lock connector having a central tubular portion defining an axial bore with at least a portion of said central tubular portion being enclosed by an outer sheath having a generally circular cross-sectional configuration;

said outer sheath having internal connecting means for cooperating with external connecting means of said female luer lock connector;

said female luer lock connector comprising a main tubular member for receiving said central tubular portion and having said external connecting means for cooperating with the internal connecting means of said male luer connector's outer sheath;

said main tubular member of said female luer connector having visual indicating means which is positioned to indicate that the male and female connectors are assembled properly for use when said outer sheath and said visual indicating means are in a predetermined relationship, said visual indicating means comprising an outwardly extending member adapted for engagement with said outer sheath when said male and female connectors are assembled properly;

said predetermined relationship comprising an overdriven position of said main tubular member with respect to said central tubular portion, said central tubular portion being tapered outwardly rearwardly to form a sealing area with said main tubular member but having no taper at an area corresponding to the overdriven position area.

* * * * *